US00PP19244P2

(12) United States Plant Patent
Pierce

(10) Patent No.: US PP19,244 P2
(45) Date of Patent: Sep. 16, 2008

(54) ***CALIBRACHOA* PLANT NAMED 'CAL LITBULE'**

(50) Latin Name: ***Calibrachoa* sp.**
Varietal Denomination: Cal Litbule

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/827,218

(22) Filed: Jul. 11, 2007

(51) Int. Cl.
*A01H 5/00* (2006.01)

(52) U.S. Cl. ..... Plt./413

(58) Field of Classification Search ..... Plt./413
See application file for complete search history.

(56) References Cited

PUBLICATIONS

UPOV ROM GTITM Computer Database, GTI Jouve Retrieval Software 2007/04 Citataion for 'Cal Litbule'.*

* cited by examiner

*Primary Examiner*—Wendy C. Haas
(74) *Attorney, Agent, or Firm*—Jondle & Associates, P.C.

(57) ABSTRACT

A new *Calibrachoa* plant particularly distinguished by large blue flowers, early and continuous flowering, deep-green foliage with elliptical leaves, good vigor, well branched, semi-upright and decumbent, later prostrate or trailing plant habit, is disclosed.

2 Drawing Sheets

Genus and species: *Calibrachoa* sp.
Variety denomination: 'Cal Litbule'.

BACKGROUND OF THE NEW PLANT

The present invention comprises a new and distinct cultivar of *Calibrachoa,* botanically known as *Calibrachoa* sp., and hereinafter referred to by the cultivar name 'Cal Litbule'. The new cultivar originated from a hybridization made in July 2002 in Gilroy, Calif. The female parent was the proprietary blue-flowered *Calibrachoa* plant '669-1' (unpatented), while the male parent was the proprietary blue-flowered *Calibrachoa* plant '677-1' (unpatented). The seeds produced by the hybridization were sown in January 2003 in Gilroy, Calif. A single plant selection was chosen for further evaluation and for asexual propagation in April 2003 in Gilroy, Calif.

The new cultivar was created in 2002 in Gilroy, Calif. and has been asexually reproduced repeatedly by vegetative cuttings and tissue culture in Gilroy, Calif., Andijk, The Netherlands and Hillscheid, Germany over a four-year period. The plant has also been trialed at Gilroy, Calif., Andijk, The Netherlands and Hillscheid, Germany. The present invention has been found to retain its distinctive characteristics through successive asexual propagations.

SUMMARY OF THE INVENTION

The following are the most outstanding and distinguishing characteristics of this new cultivar when grown under normal horticultural practices in Gilroy, Calif. and Hillscheid, Germany.

1. Medium-sized, blue flowers;
2. Deep-green foliage with elliptical leaves;
3. Good vigor and well branched;
4. Semi-upright and decumbent, later prostrate to trailing habit; and
5. An early and continuous flowering response.

DESCRIPTION OF PHOTOGRAPHS

This new *Calibrachoa* plant is illustrated by the accompanying photographs which show overall plant habit including blooms, buds, and foliage of the plant; the colors shown are as true as can be reasonably obtained by conventional photographic procedures. The photographs are of whole plants about 20-weeks old, grown in a greenhouse in the spring season in Hillscheid, Germany. The photograph of the potted plant was taken in May. The basket plants were moved outside to grow for the summer and the photograph was taken in August.

DESCRIPTION OF THE NEW CULTIVAR

Figure 1:
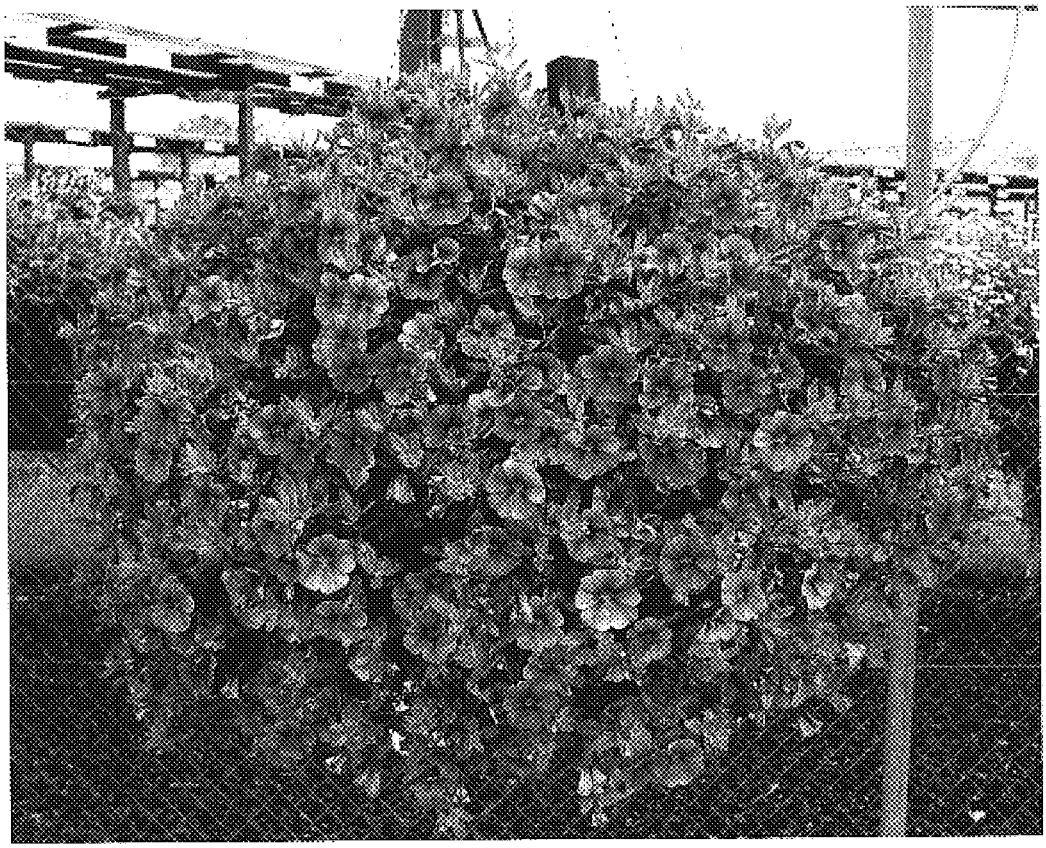
FIG. 1 shows the overall plant habit, including blooms, buds, and foliage.
Figure 2:
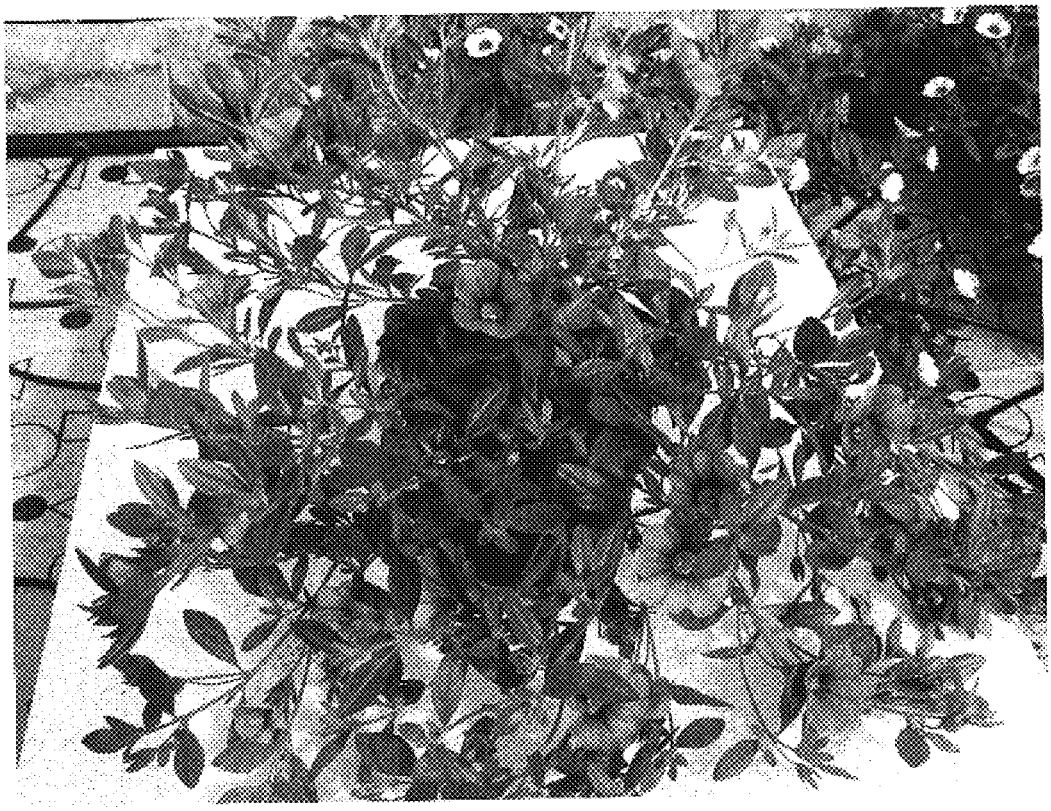
FIG. 2 shows a close-up of the mature flowers.

The following detailed description sets forth the distinctive characteristics of 'Cal Litbule'. The data which define these characteristics were collected from asexual reproductions carried out in Gilroy, Calif. The plant history was taken on 32-week old plants grown in one gallon pots in a greenhouse in the winter and spring. The plants had one plant growth regulator treatment and one terminal pinch after cuttings were transplanted to 4-inch pots and then to one gallon pots. Color readings were taken under natural light in the greenhouse. Color references are primarily to the R.H.S. Colour Chart of The Royal Horticultural Society of London (R.H.S.) (2001). Texture description data was viewed with a dissecting microscope.

DETAILED BOTANICAL DESCRIPTION OF THE NEW PLANT

Classification:
*Family.*—Solanaceae.
*Botanical.*—*Calibrachoa* sp.
*Common name.*—*Calibrachoa.*

Parentage:

*Female parent.*—'669-1' a proprietary blue-flowered *Calibrachoa* plant (unpatented).

*Male parent.*—'677-1', a proprietary blue-flowered *Calibrachoa* plant (unpatented).

Growth:

*Form.*—Semi-upright and decumbent (initially spreading to later prostrate to trailing).

*Habit.*—Good vigorous habit, well-branched, full plant; early to continuous flowering response.

*Height* (*measured from the top of the soil*).—10.0 cm to 15.0 cm.

*Width* (*horizontal plant diameter*).—50.0 cm to 60.0 cm.

*Time to produce a finished flowering plant.*—10 weeks.

*Outdoor plant performance.*—Full sun; Used as a hanging plant, in mixed container plantings, mass plantings in a bed.

*Time to initiate and develop roots.*—18 to 23 days.

*Root description.*—White, fibrous.

Stems:

*Length of basal branches.*—60.0 cm to 75.0 cm.

*Internode length.*—0.5 cm to 1.0 cm.

*Diameter of branches* (*from midpoint*).—0.2 cm.

*Stem color.*—RHS 144B.

*Texture.*—Many short glandular hairs.

*Anthocyanin.*—Present on the upper surface, very subdued hue of RHS N187A.

*Pedicel color.*—RHS 144B, with anthocyanins of subdued hue of RHS N187A at the attachment point to the corolla.

*Pedicel length.*—1.1 cm to 2.0 cm.

*Pedicel diameter.*—0.1 cm.

*Pedicel texture.*—Many short glandular hairs.

Leaves:

*Arrangement.*—Alternate; upper leaves sub-opposite.

*Size.*—Length: 2.5 cm to 2.8 cm. Width: 2.1 cm to 2.3 cm.

*Shape.*—Elliptical.

*Margin.*—Entire.

*Apex.*—Slightly rounded to slightly acute.

*Base.*—Acuminate.

*Color.*—Immature: Upper surface: RHS 137B to RHS 137C. Lower surface: RHS 137C. Mature: Upper surface: RHS 137A, but darker. Lower surface: RHS 137C.

*Texture.*—Short glandular hairs.

*Venation.*—Pinnate.

*Venation color.*—RHS 144B mainly at midrib, otherwise indistinct.

*Variegation.*—None.

*Petioles.*—Length: 0.3 cm to 0.4 cm. Width: 0.1 cm. Color: RHS 144B. Texture: Short glandular hairs.

Flower bud:

*Shape.*—Oblong.

*Size.*—Length: 1.5 cm to 2.3 cm. Diameter: 0.5 cm.

*Color at tight bud.*—RHS N81B.

Inflorescence:

*Blooming habit.*—Continuous throughout the growing season; good floriferousness.

*Inflorescence type.*—Flowers solitary in upper leaf axis.

*Floret type.*—Funnel form; 5 lobed petals, fused at base.

*Number of flowers per node.*—1.

*Lastingness of individual blooms on the plant.*—5 to 8 days.

*Fragrance.*—Absent.

Flowers:

*Immature flower.*—Diameter: Horizontal: 3.0 cm to 3.5 cm. Vertical: 2.7 cm to 2.9 cm. Color: Upperside: RHS N82B; RHS N82A at the corolla tube opening; RHS N81A veins. Lowerside: RHS 76C with some overlay of irregular patches of RHS 77B; RHS 79A mid-veins; RHS 79D veins.

*Mature flower.*—Diameter: Horizontal: 3.7 cm to 4.2 cm. Vertical: 3.4 cm to 3.6 cm. Color: Upperside: RHS N82B then fading to RHS N82C to RHS N82D; RHS N82A at the corolla tube opening; RHS N81A veins. Lowerside: RHS 76C with some overlay of irregular patches of RHS 77B; RHS 79A mid-veins; RHS 79D veins.

*Corolla tube.*—Color inside: RHS 12A; RHS N77C veins. Color outside: RHS 8B to RHS 8C basally; RHS N77B at the corolla tube opening; RHS N77A mid-veins and RHS N77C veins. Tube length: 1.5 cm to 1.7 cm. Outside texture: Glandular hairs of various sizes.

*Petals.*—Apex: Slightly emarginate. Base: Fused. Margin: Entire. Waviness of petals: Moderate. Lobation: Moderate. Texture: Papillose with glandular hairs at the margin.

*Sepals.*—Calyx: 5 sepals fused at base and somewhat outwardly reflexing. Shape: Oblong. Apex: Obtuse to slightly acute. Base: Fused. Margin: Entire. Length: 1.3 cm to 1.6 cm. Width: 0.3 cm. Color: RHS 137B; RHS 137A at the apex. Texture: Glandular hairs mainly on the mid-vein.

Reproductive organs:

*Stamens.*—Number: 5; 2 long, 3 short. Filament color: RHS 3D. Filament length: 0.8 cm to 1.1 cm. Filament diameter: Less than 0.1 cm. Pollen color: RHS 3C. Pollen quantity: Moderate.

*Pistils.*—Number: 1. Length: 1.0 cm. Diameter: 0.1 cm. Stigma color: RHS 145A. Style color: RHS 145C.

Fruit and seed set: Not observed.

Disease and insect resistance: No particular resistance or susceptibility has been observed.

COMPARISON WITH PARENTAL AND COMMERCIAL CULTIVARS

'Cal Litbule' differs from the female parent '669-1' (unpatented) by having light blue flowers, while the female parent has blue flowers. Additionally, 'Cal Litbule' is earlier to flower and has more basal branches than '669-1'.

'Cal Litbule' differs from the male parent '677-1' (unpatented) by having light blue flowers while '677-1' has blue flowers. Additionally, 'Cal Litbule' has darker green leaves and larger flowers than '677-1'.

'Cal Litbule' differs from the commercial cultivar 'Sunbel-Iabu' (U.S. Plant Pat. No. 16,285) by having darker, light blue flowers as well as larger flowers than 'Sunbel-Iabu'. Additionally, 'Cal Litbule' has larger and deeper green leaves than 'Sunbel-Iabu'.

I claim:

1. A new and distinct cultivar of *Calibrachoa* plant as shown and described herein.

* * * * *